United States Patent [19]
Giudicelli et al.

[11] 3,966,745
[45] June 29, 1976

[54] VINVAMINE SERIES CYCLOALKYL-ALKYL ESTERS

[75] Inventors: Don Pierre René Lucien Giudicelli, Fontenay-sous-Bois; Henry Najer, Paris; Bogdan Iliesco-Branceni, Paris; Yves Robert Alain Pascal, Paris, all of France

[73] Assignee: Synthelabo, Paris, France

[22] Filed: May 6, 1974

[21] Appl. No.: 467,596

[30] Foreign Application Priority Data
May 7, 1973 France .............................. 73.16266

[52] U.S. Cl............................. 260/293.53; 424/267
[51] Int. Cl.².......................................... C07D 519/04
[58] Field of Search.................... 260/287 R, 293.53

[56] References Cited
UNITED STATES PATENTS

| | | | |
|---|---|---|---|
| 3,852,453 | 12/1974 | Guidicelli et al. | 424/262 |
| 3,891,640 | 6/1975 | Plat et al. | 260/293.53 |

*Primary Examiner*—Alton D. Rollins
*Assistant Examiner*—David E. Wheeler
*Attorney, Agent, or Firm*—Armstrong, Nikaido & Wegner

[57] ABSTRACT

Compounds of the general formula

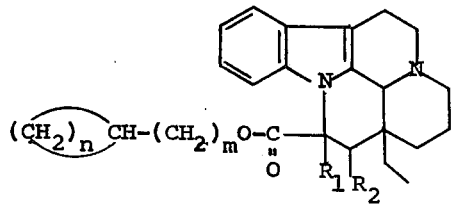

wherein $R_1$ is H or OH and $R_2$ is H or $R_1$ and $R_2$ together represent an additional double bond between the two carbon atoms to which they are attached and $m$ and $n$ are integers of 1 to 5 and 2 to 7 respectively; and pharmaceutically acceptable acid addition salts thereof. The compounds are useful for the treatment of vascular disorders in mammals.

7 Claims, No Drawings

VINVAMINE SERIES CYCLOALKYL-ALKYL ESTERS

The present invention relates to new cycloalkylalkyl esters of acids derived from eburnamine, and pharmaceutically acceptable acid addition salts thereof.

According to the present invention there are provided compounds of the general formula (I)

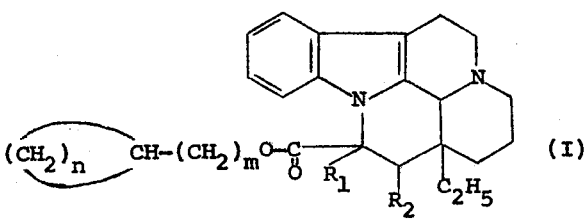

wherein:

$R_1$ represents a hydrogen atom or a hydroxyl group and $R_2$ represents a hydrogen atom, or $R_1$ and $R_2$, together represent an additional bond between the two carbon atoms to which they are attached, $m$ is an integer of 1 to 5, and $n$ is an integer of 2 to 7; or a pharmaceutically acceptable acid addition salt thereof.

All the stereoisomeric forms of these esters and of their salts also form part of the invention.

The invention also provides a process for the preparation of the esters (I) and their salts which process comprises converting a compound of the formula (II)

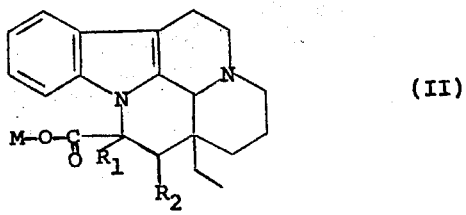

wherein $R_1$ and $R_2$ are as hereinbefore defined and M is a hydrogen atom, an alkali metal or a lower alkyl group, to a compound of the formula (I) and if desired, when $R_1$ is a hydroxyl group and $R_2$ is a hydrogen atom, also subjecting the compound to dehydration to form a compound of general formula (I) wherein $R_1$ and $R_2$ together represent an additional bond between the two carbon atoms to which they are attached; and further, if desired, reacting the resultant compound with a pharmaceutically acceptable organic or inorganic acid to form a salt.

The conversion of the compounds of general formula (II) into the esters (I) of the present invention can be accomplished by using any known method, especially:

1. By esterification of the corresponding acid or one of its salts, in an alkaline medium, using a cycloalkylalkyl halide. The reaction is preferably carried out in an apolar solvent such as dimethylformamide or hexamethylphosphorotriamide or a mixture of solvents of this nature, at 50° to 150°C.

2. By conversion of a simple ester of the corresponding acid (e.g. a methyl ester such as vincamine, apovincamine or desoxyvincamine) to a cycloalkylalkyl ester, using a conventional transesterification process.

3. When $R_1$ and $R_2$ represent an additional double bond (i.e. in apovincamine derivatives and their stereoisomers), by esterification of vincaminic acid or its stereoisomers (Formula II: M=H, $R_1$ = OH and $R_2$ = H) with simultaneous or subsequent dehydration.

The compounds of the invention are useful as pharmaceuticals for the treatment of humans or for use in veterinary therapy, especially for the treatment of vascular disorders and more especially cerebral disorders.

The compounds are especially useful as vasodilators and cerebral oxygen economisers.

They can be administered orally, endorectally or parenterally.

Oral administration is usually effected by means of any suitable pharmaceutical form especially tablets which can be converted into dragees or can be coated, capsules or gelatin-coated pills, the active principle being combined with the usual excipients for these medicinal forms. A unit dose usually contains 1 to 20 mg. of active compound.

Endorectal administration is normally effected at a dose of 1 to 40 mg, the active principle being distributed throughout any base conventionally used for suppositories.

The maximum daily dose in both the above methods is 80 mg.

Parenteral administration is usually effected at a dose of 0.20 to 15 mg, the active principle being dissolved or suspended in any physiologically tolerated buffered solution. The maximum daily dose is normally 10 to 60 mg.

Thus the present invention also provides pharmaceutical compositions comprising a compound of general formula (I) and a pharmaceutically acceptable carrier or diluent.

The following Examples serve to further illustrate the invention.

EXAMPLE 1

Cyclopropylmethyl vincaminate and its tartrate (Formula I: $R_1$ = OH, $R_2$ = H, $n$ = 2 and $m$ = 1; SL 72-401)

Sodium hydride (as 50% by weight dispersion in mineral oil) (1g; 0.021 mol) was added in small portions, with stirring under nitrogen, to a solution of vincaminic acid (6.8 g; 0.02 mol) in dimethylformamide (25 ml). This mixture was stirred at ambient temperature until hydrogen ceased to be evolved (approximately 1 hour), and cyclopropylmethyl bromide (13.5 g; 0.1 mol) was then added. The reaction mixture was heated gradually to 70°–80°C, and this temperature was maintained for two hours. The reaction mixture was cooled and poured into water and the resultant mixture was extracted with ethyl acetate. The organic layer was separated, washed with water, dried over sodium sulphate and filtered. The solvent was evaporated from the filtrate and the residue was recrystallised from alcohol to give cyclopropylmethyl vincaminate (4.5 g; yield = 57%), m.p. 120°C.

Analysis: $C_{24}H_{30}N_2O_3$ (M.W. = 394.5) Calculated %: C 73.20 H 7.62 N 7.11. Found %: 73.29 7.84 7.02.

The tartrate of this amino-ester was prepared by mixing equimolecular amounts of tartaric acid and the aminoester in alcoholic solution. The tartrate which precipitated was filtered off and recrystallised from alcohol; melting point = 123°C.

Analysis: $C_{28}H_{36}N_2O_9$ (M.W. = 544.5). Calculated %: C 61.8 H 6.63 N 5.15. Found %: 61.36 7.05 5.09.

EXAMPLE 2

Cyclopropylmethyl apovincaminate and its tartrate (Formula I: $R_1$ and $R_2$ form an additional bond, $n = 2$ and $m = 1$; SL 73-005)

a. Sodium hydride (as 50% by weight dispersion in mineral oil) (1.7 g; 0.035 mol) was added slowly to a solution of apovincaminic acid (10 g; 0.031 mol) in anhydrous dimethylformamide (50 ml) under nitrogen. This mixture was stirred at ambient temperature until hydrogen ceased to be evolved. After adding cyclopropylmethyl bromide (4.2 g; 0.031 mol), the reaction mixture was heated whilst stirring for 4 hours at 100°C; cooled and poured onto ice. Ammonium chloride was added to obtain a slightly alkaline mixture and the mixture was then extracted with ethyl acetate. The organic layer was isolated, washed with water, dried over sodium sulphate and filtered, and the solvent was evaporated from the filtrate. An oil which could not be distilled or crystallised was obtained.

The oil was purified by converting it to the oxalate, precipitating the oxalate from ethyl acetate, and recrystallising it from water. This oxalate was dissolved in water, the solution was rendered alkaline and extracted with ethyl acetate. The ethyl acetate solution was washed with water, dried over sodium sulphate and filtered; the solvent was evaporated, and the resultant purified oily amino-ester was converted to the tartrate by mixing equimolecular amounts of the aminoester and tartaric acid in methanol, from which it separates out to give cyclopropylmethyl apovincaminate tartrate (8 g; yield = 50%), m.p. 110°C.

Analysis: $C_{28}H_{34}N_2O_8$ (M.W. = 526.5). Calculated %: C 63.88 H 6.51 N 5.32. Found %: 63.46 6.59 5.55.

b. Sodium hydride (as a 50% by weight dispersion in mineral oil) (3 g; 0.062 mol) was added to a solution of vincaminic acid (13.6 g; 0.04 mol) in hexamethylphosphorotriamide (50 ml). The mixture was heated on an oil bath, with stirring, at 130°–140°C until a clear solution was obtained. Cyclopropylmethyl bromide (5.4 g; 0.04 mol) was added and heating was continued for 3 hours at 140°C.

The product was isolated and purified as described in (a) above to yield cyclopropylmethyl apovincaminate tartrate (10 g; yield = 47.5%).

EXAMPLE 3

Cyclopropylmethyl desoxyvincaminate and its tartrate (Formula I: $R_1 = R_2 = H$, $n = 2$ and $m = 1$; SL 73-041)

A solution of potassium hydroxide (1.82 g; 0.0325 mol) in methanol (18 ml) was added to a solution of desoxyvincamine (10 g; 0.0296 mol) in methanol (100 ml) and the mixture was stirred for 16 hours at ambient temperature. The mixture was evaporated to dryness and the residue was washed several times with a little benzene to give the dry potassium salt. A reddish resin, shown by its I.R. spectrum to be potassium desoxyvincaminate, was obtained in quantitative yield.

A solution of cyclopropylmethyl bromide (3.32 g; 0.0238 mol) in dimethylformamide (15 ml) was added dropwise while stirring under nitrogen to a solution of potassium desoxyvincaminate (8.6 g; 0.0238 mol) in dimethylformamide (35 ml). The mixture was heated for 24 hours at 100°C; the reaction mixture was cooled, poured into water (500 ml) and extracted several times with ether. The organic extracts were combined, washed with water, dried over sodium sulphate and filtered, and the solvent was evaporated to give cyclopropylmethyl desoxyvincaminate (9.5 g) as a chromatographically pure uncrystallisable oil.

A solution of cyclopropylmethyl desoxyvincaminate (9 g; 0.024 mol) in ethanol (9 ml) was added to a solution of tartaric acid (3.6 g; 0.024 mol) in ethanol (10 ml). The mixture was stirred for 10 minutes and ether (200 ml) was then added slowly with stirring. The tartrate precipitated in the form of a gum. The solvent was decanted and the gum was triturated with ether until crystallisation occurred. The crude tartrate (11.2 g) thus obtained was purified by dissolving it in boiling chloroform (30 ml) and by adding hexane (300 ml) to the solution. On cooling, the salt separates out as solid cyclopropylmethyl desoxyvincaminate tartrate (10.8 g; yield = 86.7%) m.p. 130°C.

Analysis: $C_{28}H_{36}N_2O_8$ (528.5). Calculated % : C 63.62 H 6.86 N 5.30 O 24.21. Calculated (including 1.42% $H_2O$). (determined by the Karl Fishcher method) : C 62.71 H 6.89 N 5.22 O 25.13. Found % : 62.16 6.95 5.23 25.19.

The new compounds were subjected to pharmacological tests which demonstrated their valuable properties, especially their effect on circulation and cerebral oxygenation.

Acute toxicity

The tests were carried out on mice of the Swiss strain of both sexes, each weighing 20 g on average. The $LD_{50}$'s were calculated in accordance with the method of Miller and Tainter (Proc. Soc. exp. Biol. Med., 1944, 57, 261).

The results are given in Table I.

TABLE I

| Compounds | $LD_{50}$ mg/kg - intraperitoneal administration |
|---|---|
| SL 72-401 | 220 |
| SL 73-005 | 380 |
| SL 73-041 | 260 |
| Vincamine | 215 |

Hypobaric anoxia in mice

The mice are kept in an atmosphere which is depleted in oxygen by creating a partial vacuum. The degree of anoxia was chosen after preliminary tests. The survival time of the control and treated animals is noted.

The chamber into which the animals are introduced is a chemical desiccator, divided into 7 compartments. Calcium oxide is placed in this chamber in order to absorb the expired carbon dioxide. This desicator is connected to a vacuum pump and to a manometer to measure the residual pressure.

Ten minutes before introducing the mice (male mice of the Swiss strain, each weighing approximately 20 g)

into the chamber, they are treated, generally by intraperitoneal injection, with the substances to be tested. The treatment involves the injection, generally intraperitoneally, of different doses of the test substances as solution in physiological serum in the presence of ascorbic acid (two parts of ascorbic acid for one part of the substance).

The injections are carried out using a volume of 0.5 ml per 20 g of body weight.

7 animals are introduced at the same time into the chamber, i.e. 1 control mouse (treated with physiological serum), 3 mice each treated with a different dose of a reference substance, and three mice each treated with a different dose of a test substance.

The chamber is then evacuated until the residual pressure therein is 19 cm of Hg (this is achieved in approximately 30 seconds).

The survival time i.e. the time until the animals stop breathing of each of the animals is then recorded. Under these conditions, the average survival time of the control animals is approximately 75 seconds. The percentage increases are calculated from values obtained for each batch of animals.

The results are given in Table II, and show the mean active doses (MAD), that is to say the dose which increases the survival time of the animals by 100%.

The reference substance was vincamine.

TABLE II

| Compounds | MAD, intraperitoneal administration | |
|---|---|---|
| | Absolute value mg/kg | Molecular equivalent of vincamine |
| SL 72-401 | 11 | 7 |
| SL 73-005 | 6 | 4 |
| SL 73-041 | 6 | 4 |
| Vincamine | 8 | 8 |

It is thus seen that, on a molecular basis, all the tested compounds of the invention have an activity which is greater than that of vincamine, and that on a weight basis, two of them are more active than vincamine. Moreover, the therapeutic indices of the compounds SL 73-005 and SL 73-041 are respectively 2.5 and 1.6 times more favourable than that of vincamine.

We claim:
1. A compound of the formula

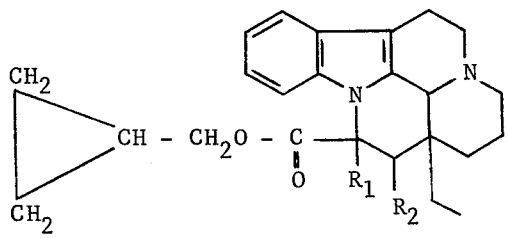

wherein
$R_1$ is hydrogen or hydroxy:
$R_2$ is hydrogen, or
$R_1$ and $R_2$ together represent an additional bond between the two carbon atoms to which they are attached, or a pharmaceutically acceptable acid addition salt thereof.

2. A compound as claimed in claim 1 which is cyclopropylmethyl vincaminate or its tartrate.

3. A compound as claimed in claim 1 which is cyclopropylmethyl apovincaminate or its tartrate.

4. A compound as claimed in claim 1 which is cyclopropylmethyl desoxyvincaminate or its tartrate.

5. A compound as claimed in claim 1 which is cyclopropylmethyl vincaminate ascorbate.

6. A compound as claimed in claim 1 which is cyclopropylmethyl apovincaminate ascorbate.

7. A compound as claimed in claim 1 which is cyclopropylmethyl desoxyvincaminate ascorbate.

* * * * *